US012678428B2

(12) United States Patent
Samant et al.

(10) Patent No.: US 12,678,428 B2
(45) Date of Patent: Jul. 14, 2026

(54) SYNERGISTIC COMPOSITION FOR INHIBITING VASCULAR CALCIFICATION

(71) Applicant: Celagenex Research (India) Pvt. Ltd., Thane West (IN)

(72) Inventors: Rajaram Samant, Thane West (IN); Rajendra Prasad T., Rajasthan (IN); Jotiram Palkar, Thane West (IN)

(73) Assignee: CELAGENEX RESEARCH (INDIA) PVT. LTD., Maharashtra (IN)

( * ) Notice: Subject to any disclaimer, the term of this patent is extended or adjusted under 35 U.S.C. 154(b) by 355 days.

(21) Appl. No.: 18/571,050

(22) PCT Filed: Jun. 15, 2022

(86) PCT No.: PCT/IN2022/050545
§ 371 (c)(1),
(2) Date: Dec. 15, 2023

(87) PCT Pub. No.: WO2022/264167
PCT Pub. Date: Dec. 22, 2022

(65) Prior Publication Data
US 2024/0277681 A1 Aug. 22, 2024

(30) Foreign Application Priority Data
Jun. 15, 2021 (IN) ............................. 202121017568

(51) Int. Cl.
*A61K 31/4412* (2006.01)
*A61K 9/00* (2006.01)
*A61K 31/185* (2006.01)

(52) U.S. Cl.
CPC ........ *A61K 31/4412* (2013.01); *A61K 31/185* (2013.01); *A61K 9/0053* (2013.01)

(58) Field of Classification Search
CPC .............. A61K 31/4412; A61K 31/185; A61K 9/0053; A61K 9/4866; A61K 9/2027
See application file for complete search history.

(56) References Cited

U.S. PATENT DOCUMENTS

| | | | |
|---|---|---|---|
| 6,521,645 B2 | 2/2003 | Voziyan et al. | |
| 6,716,858 B1 | 4/2004 | Khalifah et al. | |
| 2018/0214463 A1 | 8/2018 | Grases Freixedas et al. | |

FOREIGN PATENT DOCUMENTS

| | | |
|---|---|---|
| FR | 2878160 A1 | 5/2006 |
| WO | 2000023063 A2 | 4/2000 |
| WO | 2007053700 A2 | 5/2007 |

OTHER PUBLICATIONS

Pouteau et al. Superiority of magnesium and vitamin B6 over magnesium alone on severe stress in healthy adults with low magnesemia: A randomized, single-blind clinical trial; (PLOS ONE, 2018, 1-17). (Year: 2018).*

Stubbs, Jason, "Role of Fibroblast Growth Factor 23 in Phosphate Homeostasis and Pathogenesis of Disordered Mineral Metabolism in Choronic Kidney Disease", Semin Dial. Jul.-Aug. 2007;20(4):302-8.

Braake, Anique, "Magnesium Counteracts Vascular Calcification Passive Interference or Active Modulation?", Arterioscler Thromb Vasc Biol. 2017; 37: 1431-1445.

Braake, Anique, "Calciprotein particle inhibition explains magnesium-mediated protection against vascular calcification", Nephrology Dialysis Transplantation (May 2020) vol. 35: Issue 5, pp. 765-773.

Silva, Ana Paula, "Low Magnesium Levels and FGF-23 Dysregulation Predict Mitral Valve Calcification as well as Intima Media Thickness in Predialysis Diabetic Patients", International Journal of Endocrinology vol. 2015, Article ID 308190.

Jimbo, Rika, "Fibroblast growth factor 23 accelerates phosphate-induced vascular calcification in the absence of Klotho deficiency", Kidney International May 2014; 85(5): 1103-1111.

Pescatore, Luciana, "Multifaceted Mechanisms of Vascular Calcification in Aging", Arteriosclerosis, Thrombosis, and Vascular Biology. 2019; 39:1307-1316.

Braake, Anique, "Magnesium prevents vascular calcification in Klotho deficiency", Kidney Int Mar. 2020;97(3):487-501.

Bressendorff, Iain, "The effect of magnesium supplementation on vascular calcification in chronic kidney disease- a randomized clinical trial (MAGICAL-CKD): essential study design and rationale", BMJ Open. 2017; 7(6): e016795.

Diaz-Tocados, Juan M., "Dietary magnesium supplementation prevents and reverses vascular and soft tissue calcifications in uremic rats", Basic Research, vol. 92, Issue 5, p. 1084-1099, 2017.

Mathieu R. Brodeur et al., "Reduction of Advanced-Glycation End Products Levels and Inhibition of RAGE Signaling Decreases Rat Vascular Calcification Induced By Diabetes", PLoS One, Jan. 2014, vol. 9, Issue 1, e85922.

Kay, Amber M., "The Role of AGE/RAGE Signaling in Diabetes-Mediated Vascular Calcification", Journal of Diabetes Research vol. 2016, Article ID 6809703, 8 pages.

Vallejo, Ricardo, "Modulation of neuroglial interactions using differential target multiplexed spinal cord stimulation in an animal model of neuropathic pain", Mol Pain. 2020; 16.

(Continued)

*Primary Examiner* — Kamal A Saeed
*Assistant Examiner* — Meghan C Heasley
(74) *Attorney, Agent, or Firm* — Armstrong Teasdale LLP

(57) ABSTRACT

The invention disclosed herein relates to synergistic bioactive compositions for inhibiting vascular calcification. Particularly, the present invention relates to exogenous blend of magnesium 2-acetylamino ethane sulfonic acid and 2-methyl-4-aminomethyl-5-hydroxymethyl-3-pyridinol and salts thereof which are present in the weight ratio of 1:0.002 to 1:1.8 along with pharmaceutically acceptable excipients. More particularly, the synergistic composition is useful for treating cardiovascular diseases and renal vascular diseases.

5 Claims, 1 Drawing Sheet

(56)  References Cited

OTHER PUBLICATIONS

International Search Report and ,Written Opinion issued in International Patent Application No. PCT/IN2022/050545, dated Sep. 28, 2022, 8 pages.

Anique D.ter Braake et al, "Magnesium prevents vascular calcification in vitro by inhibition of hydroxyapatite crystal formation", Sci Rep. 2018; 8: 2069.

* cited by examiner

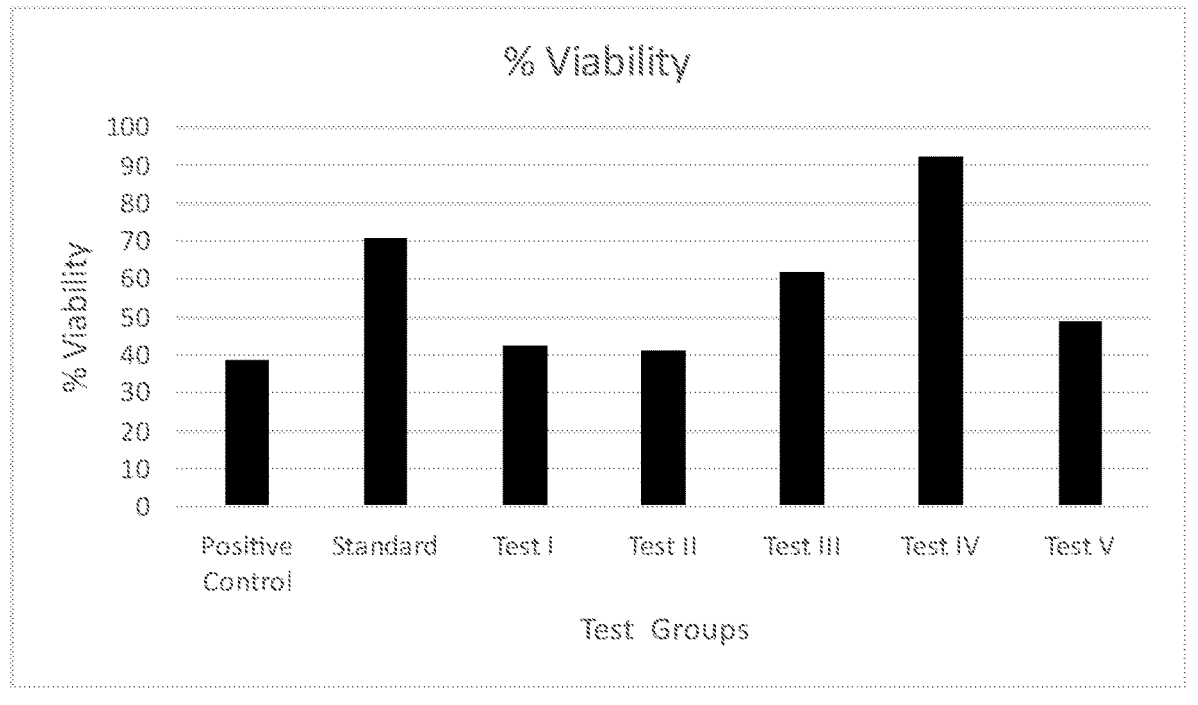

1

SYNERGISTIC COMPOSITION FOR INHIBITING VASCULAR CALCIFICATION

TECHNICAL FIELD

The present invention relates to a synergistic composition for inhibiting vascular calcification. Particularly, the present invention relates to complex comprising a synergistic combination of magnesium 2-acetylamino ethane sulfonic acid and 2-methyl-4-aminomethyl-5-hydroxymethyl-3-Pyridinol or its salts along with at least one pharmaceutically acceptable excipients. More particularly, the synergistic composition is useful for treating cardiovascular diseases and renal vascular disease.

BACKGROUND AND PRIOR ART

Vascular calcifications are deposition of minerals on the walls of arteries and veins. These mineral deposits stick to fatty deposits, or plaques which have already built up on the walls of a blood vessel.

Most individuals above the age of 60 have progressively enlarging deposits of calcium mineral in their major arteries. This vascular calcification reduces aortic and arterial elastance, which impairs cardiovascular hemodynamics, resulting in substantial morbidity and mortality. Vascular calcification, a hallmark of aging, is accelerated in patients with hypertension, diabetes, and chronic kidney disease.

Particularly, there are four main types of vascular calcification which depend on the location of the body. Vascular calcifications are classified into atherosclerotic intimal calcification, medial artery calcification (Mönckeberg's sclerosis), cardiac valve calcification, and calcific uremic arteriolopathy.

Medial calcifications are most often associated with kidney disease, diabetes, hypertension, and advanced age. Intimal calcifications are associated with blocked arteries and blood clots. Arterial calcification can occur in both intimal and medial layers. Intimal, atherosclerotic calcification can lead to myocardial infarction from stenosis and acute thrombus, or ischemia in both coronary and peripheral arteries. Medial layer calcification can lead to thickening of the medial layer of larger elastic arteries resulting in arteriosclerosis of smaller elastic arteries called medial calcinosis which is most common in patients with diabetes, renal failure and advanced aging and is associated with increased cardiovascular mortality in diabetic patients without CKD and in CKD patients with and without diabetes. Vascular calcification can occur in nearly all arterial beds and in both the medial and intimal layers. Calcium is the most common element in the bone, and 99% of the total body calcium is found in the bone in the form of a calcium phosphate crystalline structure called hydroxyapatite. Deposition of hydroxyapatite minerals into the extracellular matrix led to hardening of the medial layer of the artery.

Further, vascular calcification is highly associated with cardiovascular disease mortality and also in high-risk patients with diabetes and chronic kidney diseases (CKD). In blood vessels, intimal calcification is associated with atherosclerosis and medial calcification is a non-occlusive process which leads to increased vascular stiffness and reduced vascular compliance. In the valves, calcification of the leaflets can change the mechanical properties of the tissue and result in stenosis. For many decades, vascular calcification has been noted as a consequence of aging. Studies now confirm that vascular calcification is an actively regulated process and also shares many features with bone development and metabolism.

In the general population, the presence of coronary artery calcification increases cardiovascular risk above that predicted by traditional risk factors, suggesting the presence of non-traditional risk factors. The traditional risk factors are hypertension, diabetes, dyslipidaemia, age, genetics, and smoking. The non-traditional risk factors are inflammation, oxidative stress, advanced glycation end product (AGE), abnormal mineral metabolism, and FGF23 (Fibroblast growth factor 23).

Fibroblast Growth factor 23 (FGF23) is a circulatory peptide secreted by osteocytes that plays a key role in the control of serum phosphate, vitamin D metabolism and secondary hyperparathyroidism. FGF23 inhibits phosphate reabsorption in the proximal tubules and inhibits 1-α hydroxylase activity resulting in decreased calcitriol and decreased phosphate reabsorption in the intestine. FGF23 requires a co-receptor, Klotho, a single-pass transmembrane protein for activity as FGF23 is considered to only be active in tissues that also contain Klotho (distal tubule of kidney, parathyroid glands, brain). FGF23 levels increase early in the course of kidney disease in order to keep serum phosphorus within the normal range. [*Semin Dial.* 2007 July-August; 20(4):302-8.].

Over the past few years, an increasing number of observational patient studies have reported a close relationship between serum magnesium ($Mg^{2+}$) concentration and cardiovascular mortality in End-Stage Renal Disease (ESRD). A substantial number of in vitro and in vivo studies have identified a protective role for magnesium in vascular calcification. However, the precise mechanisms and its contribution to cardiovascular protection remain unclear. However, currently there are two leading hypotheses. First, magnesium may bind to phosphate and delay calcium phosphate crystal growth in the circulation, thereby passively interfering with calcium phosphate deposition in the vessel wall. Second, magnesium may regulate vascular smooth muscle cell trans-differentiation toward an osteogenic phenotype by active cellular modulation of factors associated with calcification. [*Arterioscler Thromb Vasc Biol.* 2017; 37: 1431-1445]

Currently, CKD treatment options are limited and vascular calcification continues to be a clinical problem. In the past years, several epidemiological studies have shown that a lower serum magnesium ($Mg^{2+}$) status is independently associated with an increased risk of vascular calcification and cardiovascular mortality in CKD patients. Therefore, it is hypothesized that $Mg^{2+}$ could be an effective tool to limit vascular calcification. Hydroxyapatite- and protein-containing calciprotein particles (CPPs) are major drivers of calcification.

$Mg^{2+}$ supplementation prevents Pi-induced calcification in VSMCs. $Mg^{2+}$ dose-dependently delayed the maturation of primary CPP1 to CPP2 in vitro. [*Nephrology Dialysis Transplantation* (May 2020) Volume 35: Issue 5, Pages 765-773].

Interestingly, low magnesium levels and FGF-23 dysregulation can cause mitral valve calcification as well as intima media thickness in predialysis diabetic patients. Mitral valve calcification and intima media thickness (IMT) are common complications of chronic kidney disease (CKD) implicated with high cardiovascular mortality. [*International Journal of Endocrinology* Volume 2015, Article ID 308190]

Fibroblast growth factor 23 accelerates phosphate-induced vascular calcification in the absence of Klotho deficiency. Fibroblast growth factor (FGF23) is a phosphate regulating hormone that acts primarily on the kidney and parathyroid. With declining kidney function there is an increase in circulating FGF23 levels, which is associated with vascular calcification and mortality in chronic kidney disease. Moreover, Fibroblast growth factor 23 (FGF23) enhanced phosphate-induced calcification in Klotho-over-expressing vascular smooth muscle cells and increased osteoblastic marker expression. Thus, FGF23 enhances phosphate-induced vascular calcification by promoting osteoblastic differentiation involving the ERK1/2 pathway. [*Kidney International* 2014 May; 85(5):1103-1111].

In the absence of Klotho deficiency, enhanced FGF-23 has shown to increase VSMC calcification induced by Pi.

Moreover, it is well established that, in humans, FGF-23 increases according to CKD progression. Conversely, simultaneous FGF-23 resistance may occur by decreased expression of Klotho and FGF-receptor in CKD. In addition, other studies suggest that Klotho protective effect in VC may occur by influencing oxidative stress signaling. Many studies showed that Klotho modulates mitochondrial function and increases antioxidant generation, NADPH oxidase activity, and endothelial nitric oxide synthase activation. However, further investigation is required to elucidate the impact of oxidative stress signaling involving Klotho deficiency in aging and VC. [*Arteriosclerosis, Thrombosis, and Vascular Biology.* 2019; 39:1307-1316].

It is reported that high dietary magnesium prevents calcification in Klotho knock-out mice. These effects are potentially mediated by reduction of inflammatory and extracellular matrix remodeling pathways within the aorta. Hence, magnesium treatment may be promising to prevent vascular calcification. [*Kidney Int* 2020 March; 97(3):487-501].

Anique D. ter Braake et al (Sci Rep. 2018; 8: 2069) findings demonstrate a role for Mg2+ in preventing VSMC mineralization involving direct extracellular Ca-apatite crystal inhibition.

The trial tests [BMJ Open. 2017; 7(6): e016795] disclose a new approach to the prevention of VC, by attempting to increase the uptake of a calcification inhibitor instead of limiting the uptake of a calcification promoter. Further it is observed that dietary magnesium supplementation prevents and reverses vascular and soft tissue calcifications in uremic rats. [*Basic Research*|Volume 92, Issue 5, P1084-1099, 2017.]

It is evident that magnesium prevents vascular calcification in vitro by inhibition of hydroxyapatite crystal formation. Magnesium has been shown to provide benefits against vascular calcification and low consumption of magnesium in diet has been shown to increase vascular calcification.

However, there are certain limitation with conventional Mg salts like poor bioavailability of magnesium oxide, sulphate salts limit its action in preventing vascular calcification.

Further taking large or frequent doses of dietary magnesium supplements, including magnesium glycinate, can cause adverse effects, including diarrhoea, nausea, and stomach cramps. Extremely high intakes of magnesium can lead to an irregular heartbeat and potentially a cardiac arrest, which can be dangerous.

Magnesium glycinate and other supplements might also interfere or interact with the medicines like antibiotics, bisphosphonates.

Also, the supplemental zinc can also interfere with the absorption and regulation of magnesium in the body.

Hence there is unmet need to find bioavailable salt of magnesium with no side effect and enrich with Mg content.

The present inventors have found that magnesium 2-acetylamino ethane sulfonic acid is an ideal candidate for the brain enrich source of $Mg^{2+}$. magnesium 2-acetylamino ethane sulfonic acid provides enhanced magnesium cell penetration which is rapidly absorbed.

On the other side, mere use of magnesium 2-acetylamino ethane sulfonic acid alone may not be very effective for the treatment of vascular calcification. There is a need to find out other bioactive ingredient that synergistically inhibits calcification without any side effects.

In addition to increased bone matrix protein expression in VSMCs during diabetic and calcification treatments, studies have also shown that advanced glycation end products (AGEs) and their receptors (RAGEs) play a role in vascular calcification. AGEs form over a lifetime as a result of increased circulating glucose as well as other reducing sugars, such as galactose and fructose, reacting with amino groups of proteins to form Schiff bases to either follow the polyol pathway to yield AGEs or be degraded. These glycated end products interact with RAGEs, which are transmembrane proteins part of the immunoglobulin superfamily. RAGEs are upregulated in response to increased circulating AGE levels.

Advanced-glycation end products (AGEs) were recently implicated in vascular calcification, through a process mediated by RAGE (receptor for AGEs). Inhibition of AGEs-RAGE signaling pathways can prevent calcification [*PLoS One*. 2014; 9(1): e85922].

Since formation of advanced glycation end products is one of the major factors for calcification, potent AGE-inhibitor can resolve the problems associated with vascular calcifications. Astonishingly, the present inventors have found that 4-aminomethyl form of pyridoxal is efficacious in the treatment of vascular calcification.

An animal study provides results with pyridoxamine that establishes the association between AGEs accumulation and medial calcification development. Reduction of AGEs deposition induced by pyridoxamine is associated with a profound effect on vascular calcification in the rats. [Mathieu R. Brodeur et. al. *PLoS One*, January 2014|Volume 9|Issue 1|e85922].

In studies performed by Tanikawa et al. using an HVSMC in vitro calcification model, it was found that increasing the levels of AGEs significantly increased the amount of calcium deposition after 7 and 14 days when compared to BSA treated and control samples [*Journal of Diabetes Research* Volume 2016, Article ID 6809703, 8 pages].

Pyridoxamine alleviates mechanical allodynia by suppressing the spinal receptor for advanced glycation end product-nuclear factor-κB/extracellular signal-regulated kinase signalling pathway in diabetic subjects [*Mol Pain*. 2020; 16]

Additionally, US6521645B2A discloses use of pyridoxamine for treating or preventing urinary stone disease.

US20180214463A1 describes use of phytic acid or its salts, alone or in combination, with B6 vitamers for preventing the formation of glycation end-products in diabetic patients.

WO2007053700A2 discloses use of an effective amount of pyridoxamine (PM), or an analog or derivative thereof, for ameliorating at least one symptom of a kidney disorder associated with oxidative stress, carbonyl stress, or combinations thereof in a subject.

In view of the foregoing, the inventors of the present invention have performed rigorous experiments and developed potent, non-toxic, safe and therapeutically active combination of Mg bioavailable salt and 4-aminomethyl linked active form of pyridoxal in specific ratio, where both active moieties work synergistically to reduce vascular calcification in subject in need thereof.

OBJECTIVE

The primary objective of the invention is to provide synergistic compositions for treating vascular calcification.

Another objective of the invention is to provide mineral, and vitamin based bioavailable, safe, non-toxic, compositions for preventing vascular calcification.

Yet another objective of the invention is to provide synergistic bioactive composition for treating vascular calcification through site specific action with no side effects.

SUMMARY

To meet the above objectives, the inventors of the present invention carried out thorough experiments to establish significant therapeutic effects of the active ingredients or nutrients or vitamers present in the composition for treating vascular calcification in a subject in need thereof in a safer way.

In an aspect, the invention relates to synergistic—compositions comprising therapeutically active ingredients along with pharmaceutically acceptable carriers for treating vascular calcification.

In another aspect, the invention relates to compositions comprising a synergistic combination of magnesium 2-acetylamino ethane sulfonic acid and 2-methyl-4-aminomethyl-5-hydroxymethyl-3-pyridinol and/or salts thereof along with pharmaceutically acceptable excipients.

In another aspect, the invention provides composition wherein the magnesium 2-acetylamino ethane sulfonic acid decreases urinary phosphate excretion and regulates the function of the FGF23/klotho endocrine pathways; and 2-methyl-4-aminomethyl-5-hydroxymethyl-3-pyridinol inhibits AGE-RAGE signalling. This combined therapeutic action synergistically reduces vascular calcification.

In yet another aspect, the invention relates to synergistic compositions comprising a combination of magnesium 2-acetylamino ethane sulfonic acid present in a range of 1-3000 mg, where elemental Mg may be present in the range of 1-250 mg and 2-methyl-4-aminomethyl-5-hydroxymethyl-3-pyridinol present in a range of 1-500 mg along with pharmaceutically acceptable excipients/carriers.

In another aspect, the invention relates to a synergistic composition which is useful for treatment of hypertension, cardiovascular diseases, chronic kidney diseases, diabetes, stroke, ischemia.

ABBREVIATIONS

DKD: Diabetic Kidney Diseases

ESRD: End-Stage Renal Disease

PYM: 2-methyl-4-aminomethyl-5-hydroxymethyl-3-pyridinol

VC: Vascular Calcification

VSMCs: Vascular Smooth Muscle Cells

AGE: Advanced Glycation End Product

RAGE: Receptor for Advanced Glycation End Product

FGF23: Fibroblast Growth Factor 23

CPP: Calciprotein Particles

RVD: Renal Vascular Disease

HVSMC: Human Vascular Smooth Muscle Cell

IMT: Intima Media Thickness

BRIEF DESCRIPTION OF DRAWINGS

FIG. 1 illustrates percentage of viable (live) cells in untreated and treated groups using tryphan blue exclusion assay in HaCaT cells; [Test I]—Magnesium 2-acetylamino ethane sulfonic acid—3.5 mg; [Test II]—2-methyl-4-aminomethyl-5-hydroxymethyl-3-Pyridinol—0.5 mg; [Test III]—Magnesium 2-acetylamino ethane sulfonic acid—5 mg+2-methyl-4-aminomethyl-5-hydroxymethyl-3-Pyridinol—0.02 mg; [Test IV]—Magnesium 2-acetylamino ethane sulfonic acid—0.2 mg+2-methyl-4-aminomethyl-5-hydroxymethyl-3-Pyridinol—0.2 mg; [Test V]—Magnesium 2-acetylamino ethane sulfonic acid—3.5 mg+2-methyl-4-aminomethyl-5-hydroxymethyl-3-Pyridinol—0.5 mg.

DETAILED DESCRIPTION

The present invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only and is not intended to be limiting in any manner or scope. Unless defined otherwise, all technical and scientific expressions used herein have the same meaning as commonly understood by one of ordinary skill in the art to which embodiments of the invention pertain. In describing and claiming the embodiments of the present invention, the following terminology can be used in accordance with the definitions set out below which are known in the state of art.

The singular forms "a," "an," and "the" include plural reference unless the context clearly dictates otherwise. Also, the term 'composition' does not limit the scope of the invention for multiple compositions that can be illustrated for best mode of the invention.

The term "pharmaceutically/nutraceutically acceptable salt," as used herein, represents those salts which are within the scope of sound medical judgment and suitable for use in contact with the tissues of humans and animals without undue toxicity, irritation, allergic response and the like and are commensurate with a reasonable benefit/risk ratio. Particularly, the term "pharmaceutically-acceptable salts" refer to relatively non-toxic, inorganic and organic acid addition salts of compounds, amino acid salts, sugar-based salts, alkali or alkaline earth metal salts, as well as solvates, co-crystals, polymorphs and the like of the salts.

All modifications and substitutions that come within the meaning of the description and the range of their legal equivalents are to be embraced within their scope. A description using the transition "comprising" allows the inclusion of other elements to be within the scope of the invention.

In a preferred embodiment, the invention provides a synergistic—composition for treating vascular calcification.

In another preferred embodiment, the invention provides a synergistic composition comprising a specific combination of magnesium 2-acetylamino ethane sulfonic acid and 2-methyl-4-aminomethyl-5-hydroxymethyl-3-pyridinol or salts thereof along with pharmaceutically acceptable carriers.

In one embodiment, the present biologically active composition is composed of a synergistic combination of magnesium 2-acetylamino ethane sulfonic acid and 2-methyl-4- aminomethyl-5-hydroxymethyl-3-pyridinol which are present in therapeutically effective amount. The composition significantly reduces vascular calcification while exhibiting enhanced bioavailability, solubility, and therapeutic efficacy. The improvement in vascular calcification in a subject is due to the synergistic effect of the active ingredients; wherein magnesium 2-acetylamino ethane sulfonic acid prevents the formation of hydroxyapatite and vascular smooth muscle cell mineralization by regulating function of the FGF23/klotho endocrine pathways, thereby slowing down the progression of vascular calcification; while 2-methyl-4-aminomethyl-5-hydroxymethyl-3-Pyridinol simultaneously reduces advanced-glycation end products levels and prevents calcium accumulation.

In another embodiment, the invention provides an anti-vascular calcification composition comprising a combination of an effective amount of magnesium 2-acetylamino ethane sulfonic acid along with pharmaceutically acceptable excipients.

Magnesium 2-acetylamino ethane sulfonic acid is chemically known as magnesium; 2-acetamidoethanesulfonate; dihydrate. It has a chemical formula $C_8H_{20}MgN_2O_{10}S_2$.

Moreover, Magnesium 2-acetylamino ethane sulfonic acid inhibits transformation of amorphous Ca/P to apatite. It also prevents the formation of hydroxyapatite and vascular smooth muscle cell mineralization. Magnesium 2-acetylamino ethane sulfonic acid decreases the progression of coronary artery calcification, peripheral arterial calcification, and mitral annular calcification. Magnesium 2-acetylamino ethane sulfonic acid also modulates serum FGF-23 levels and prevents vascular calcification in Klotho deficiency.

In another embodiment, the invention provides synergistic combination wherein an effective amount of Magnesium 2-acetylamino ethane sulfonic acid regulates function of the FGF23/klotho endocrine pathways and increases serum phosphorus (P) level.

Particularly, the term "elemental magnesium" as used in connection with a magnesium-counter ion compound described herein, may refer to a total amount of magnesium that is present as free ion and magnesium that is bound with one or more counter ions.

In yet another embodiment, the present invention provides a synergistic—composition comprising a therapeutically effective amount of magnesium 2-acetylamino ethane sulfonic acid or pharmaceutically acceptable salts thereof, wherein magnesium 2-acetylamino ethane sulfonic acid is present in a range of 1-3000 mg of the total composition, and wherein elemental $Mg^{2+}$ is present in the range of 1-250 mg of total composition.

In one additional embodiment, the present invention provides a synergistic composition of containing 6 to 9% w/w of elemental magnesium.

In further preferred embodiment, 100 mg to 1000 mg unit dose of magnesium 2-acetylamino ethane sulfonic acid contains 5 mg to 100 mg of elemental magnesium.

The 2-acetylamino ethane sulfonic acid salt is highly water soluble and is a bioavailable salt of magnesium which is readily absorbed in the body. Further, magnesium 2-aminoethanesulfonate levels remain high for a long time in the serum.

In yet another embodiment, the synergistic effect for treating diabetic kidney diseases is achieved by concomitant administration of another moiety along with magnesium 2-acetylamino ethane sulfonic acid. The other moiety is 2-methyl-4-aminomethyl-5-hydroxymethyl-3-pyridinol and salts thereof that effectively acts in a synergistic manner to treat vascular calcification. 2-methyl-4-aminomethyl-5-hydroxymethyl-3-pyridinol is active form of pyridoxal. 2-methyl-4-aminomethyl-5-hydroxymethyl-3-Pyridinol is a monohydroxypyridine that is pyridine substituted by a hydroxy group at position 3, an aminomethyl group at position 4, a hydroxymethyl group at position 5 and a methyl group at position 2. It has the molecular formula $C_8H_{12}N_2O_2$.

In another embodiment, the invention provides synergistic combination where 2-methyl-4-aminomethyl-5-hydroxymethyl-3-pyridinol reduces Advanced-Glycation End Products (AGEs) levels and inhibits RAGE signalling.

In another embodiment, the invention provides—composition where 2-methyl-4-aminomethyl-5-hydroxymethyl-3-pyridinol prevents calcium accumulation. 2-methyl-4-aminomethyl-5-hydroxymethyl-3-pyridinol also scavenges toxic carbonyl products of glucose and lipid degradation. 2-methyl-4-aminomethyl-5-hydroxymethyl-3-pyridinol or its salt removes or traps reactive oxygen species and form an adduct with the amadori intermediate, thereby blocking the formation of AGEs. The preferable salt of 2-methyl-4-aminomethyl-5-hydroxymethyl-3-pyridinol is its hydrochloride salt.

In another embodiment, the effective amount of 2-methyl-4-aminomethyl-5-hydroxymethyl-3-pyridinol in the present combination reduces over activation of the transcription factor Nuclear factor kappa B (NF-κB). NF-κB induces the expression of various pro-inflammatory genes, including those encoding cytokines and chemokines and also participates in inflammasome regulation.

In another embodiment, the synergistic—composition comprises a therapeutically effective amount of 2-methyl-4-aminomethyl-5-hydroxymethyl-3-pyridinol present in a range of 1-500 mg of the total composition. In yet another embodiment, 2-methyl-4-aminomethyl-5-hydroxymethyl-3-pyridinol is present in a range of 1-250 mg of the total composition.

In another embodiment, the invention provides synergistic composition wherein the composition comprises therapeutically active exogenous blend of magnesium 2-acetylamino ethane sulfonic acid and 2-methyl-4-aminomethyl-5-hydroxymethyl-3-pyridinol present in suitable weight ratio, along with pharmaceutically acceptable excipients.

More particularly, the present invention provides synergistic effects of combined magnesium 2-acetylamino ethane sulfonic acid with 2-methyl-4-aminomethyl-5-hydroxymethyl-3-pyridinol and salts thereof for inhibiting vascular calcification. The active moieties of the present composition are present in a therapeutically effective amount. The composition imparts significant effect to the subject in need thereof with enhanced bioavailability and efficacy.

In another preferred embodiment, the invention provides a stable and potent synergistic composition comprising therapeutically active exogenous combination of an effective amount magnesium 2-acetylamino ethane sulfonic acid and 2-methyl-4-aminomethyl-5-hydroxymethyl-3-pyridinol which are present in weight ratio of 1:0.002 to 1:1.8 along with pharmaceutically acceptable excipients.

In yet another preferred embodiment, the invention provides stable synergistic compositions for treating vascular calcification comprising exogenous blend of white crystalline magnesium 2-acetylamino ethane sulfonic acid and 2-methyl-4-aminomethyl-5-hydroxymethyl-3-pyridinol present in weight ratio of 1:0.002 to 1:1.8, along with pharmaceutically acceptable excipients, wherein the magnesium 2-acetylamino ethane sulfonic acid regulates function of the FGF23/klotho endocrine pathways and increases serum phosphorus (P) level and 2-methyl-4-aminomethyl-5-hydroxymethyl-3-pyridinol reduces Advanced-Glycation End Products (AGEs) levels and inhibits RAGE signalling.

In one more embodiment, the invention provides potent synergistic bioactive composition comprising white crystalline magnesium 2-acetylamino ethane sulfonic acid present in a range of 25% to 99% by weight of the total composition.

In another embodiment, the invention provides potent and stable synergistic composition comprising white crystalline 2-methyl-4-aminomethyl-5-hydroxymethyl-3-pyridinol which is present in a range of 0.1% to 60% by weight of the total composition.

In another embodiment, the invention provides potent and stable synergistic composition useful for inhibiting vascular calcification.

Particularly the vascular calcification diseases are including but not limited to treating hypertension, diabetes, chronic kidney diseases, diabetic nephropathy, coronary artery diseases, atherosclerosis or renal failure.

The term "therapeutically effective amount" denotes an amount that reduces the risk, potential, possibility or occurrence of a disease or disorder, or provides advanced alleviation, mitigation, and/or reduction or restoration or modulation, and regulation of at least one indicator/biomarker (e.g., blood or serum CRP level), and/or minimizes at least one clinical symptom related to VC.

Particularly the present synergistic composition upon oral administration of an effective dose lowers the rate of necrosis and apoptosis.

'Necrosis' is a form of cell injury which results in the premature death of cells in living tissue by autolysis. Necrosis is caused by factors external to the cell or tissue, such as infection, or trauma which result in the unregulated digestion of cell components.

'Apoptosis' is a form of programmed cell death that occurs in multicellular organisms. Biochemical changes which include blebbing, cell shrinkage, nuclear fragmentation, chromatin condensation, DNA fragmentation, and mRNA decay lead to characteristic cell changes (morphology) and death.

In yet another embodiment, the invention provides synergistic composition wherein the oral administration of the effective dose of the composition improves the cell viability by 48% to 93% as compared to individual ingredients.

In another embodiment, the invention relates to a synergistic—composition useful for the treatment of hypertension, cardiovascular diseases, chronic kidney diseases, kidney function decline, dialysis vintage, disordered mineral metabolism, elevated serum phosphate levels, elevated serum calcium levels, elevated parathyroid hormone levels, changes in vitamin D metabolism, elevated FGF 23 levels, inflammation and oxidative stress, osteogenesis factors Core-binding factor alpha(1) (Cbfa1), heart attack, heart failure, coronary artery diseases, diabetes stroke, dementia, renal insufficiency, inadequate blood supply to arms and legs, peripheral artery disease (PAD), loss of elasticity of arteries, increase in pulse pressure, development of left ventricular hypertrophy (LVH), heart failure (HF), lower coronary artery perfusion and myocardial ischemia, impaired calcium-phosphate metabolism, diastolic dysfunction, cardiac valve calcification, ischemic heart disease and episodes of cardiac failure.

The term "therapeutically effective amount" denotes an amount that reduces the risk, potential, possibility or occurrence of a disease or disorder, or provides advanced alleviation, mitigation, and/or reduction, restoration, modulation and/or minimization of at least one clinical symptom related to VC.

The term 'subject in need thereof' pertains to a subject preferably a mammal, more preferably a human suffering or suspected to be suffering from VC.

In the context of the present invention, the term "treatment" refers to alleviation, mitigation, prophylaxis, attenuation, management, regulation, modulation, control, minimization, lessening, decrease, down regulation, up regulation, moderation, curtailment, restriction, inhibition, restoration, suppression, reversal, limitation, blocking prevention, stabilization, amelioration, curing, or healing of VC.

Notably, the present synergistic composition is non-hazardous, non-toxic, and safe for human consumption without any severe adverse effects. The present medicinal composition is also used as preventive therapy/adjuvant therapy/add-on therapy/combination/adjunctive therapy in a subject in need thereof.

Certain compounds of the present invention exist in unsolvated forms as well as solvated forms, including hydrated forms. Further, some compounds of the present invention exist in multiple crystalline or amorphous forms ("polymorphs"). Compounds of the invention are formulated in geometric or, enantiomeric or stereoisomeric forms.

As used herein, the term "pharmaceutically acceptable carriers, diluents or excipients" is purported to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethyleneglycol matrix, which is acceptable for use in the subject, preferably humans. Excipients also include antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, waters of hydration, or salts.

In another embodiment, the invention relates to a synergistic medicinal composition prepared in a manner well known in the pharmaceutical art, and administered by a variety of routes, depending upon whether local or systemic treatment is desired and upon the area to be treated. The preferable route of administration includes but is not limited to sublingual, rectal, topical, parenteral, nasal, or oral.

In yet another embodiment, the present synergistic medicinal composition is administered to a subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet, capsule, film, spray. In a further embodiment, the composition is formulated for parenteral use including intravenous, subcutaneous, intramuscular, intravascular, infusion, intraperitoneal, intracerebral, intracerebroventricular, or intradermal routes of administration.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 5000 mg per day, preferably about 100 mg per day to about 1500 mg per day.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion. The active ingredients can also be presented in the form of a bolus, electuary or paste, bar, energy bars (candy bars), powder, or granule sachet.

Further, the present composition can be formulated in the form of age-appropriate paediatric oral dosage forms such as syrup, minitablets, chewable formulations, orodispersible films, or orodispersible tablets. It can also be prepared in the form of snack, chocolate bars or other confectionery food products.

In another embodiment, the synergistic composition of the present invention is non-toxic, cost effective, enriched with nutrients or biomolecules, and provides safeguard against problems associated with neurotransmission without any adverse/side effect.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, β-cyclodextrin, methylated-β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the diluent in the composition/formulation is present in a range of 1% to 30% by weight of the total composition/formulation.

In yet another embodiment, the binder is selected from disaccharides such as sucrose, lactose, polysaccharides and their derivatives like starches, cellulose, or modified cellulose such as microcrystalline cellulose and cellulose ethers such as hydroxypropyl cellulose (HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In further embodiment of the invention, the binder in the composition/formulation is present in a range of 0.1% to 40% by weight of the composition/formulation.

In a preferred embodiment of the invention, the amount of binder is present in a range of 0.1% to 25% by weight of the composition/formulation.

In some embodiment, the antioxidant is selected from tocopherol (vitamin E), sesamol, guaiac resin, methionine, beta-carotene, lycopene, lutein, zeaxanthin, butylated hydroxyanisole (BHA), butylated hydroxytoluene (BHT), sodium ascorbate, sodium metabisulfite (SMB), 1-carnosine, propyl gallate (PG), tertiary butyl hydroquinone, quercetin, resveratrol, polydatin, luteolin, thioctic acid, cysteine (CYS), citric acid, tartaric acid, phosphoric acid and ascorbic acid.

In some embodiment of the invention, the amount of antioxidant in the composition/formulation is present in the range of 0.1% to 10% by weight of the composition/formulation.

In a preferred embodiment of the invention, the amount of antioxidant is present in a range of 0.1% to 5.0% by weight of the composition/formulation.

In another embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In some embodiment of the invention, the lubricant in the composition/formulation is present in a range of 0.1% to 10.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, phosphatidylcholine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxpropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In another embodiment of the invention, the amount of solubilizing agent or surfactant in the composition/formulation ranges from 0.1% to 10% by weight of the composition/formulation.

In a preferred embodiment of the invention, the solubilizing agent or surfactant is present in a range of 0.1% to 5.0% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In some embodiment of the invention, the stabilizer in the composition/formulation is present in a range of 0.1% to 8.0% by weight of the total composition/formulation.

In a preferred embodiment of the invention, the amount of stabilizer is present in a range of 0.1% to 5.0% by weight of the composition/formulation.

In some embodiment of the invention, the plasticizers are added to coating formulations selected from the group propylene glycol, glycerol, glyceryl triacetate (triacetin), triethyl citrate, acetyl triethyl citrate, diethyl phthalate, actetylated monoglycerides, castor oil, mineral oil and like thereof. In some embodiment of the invention, the plasticizer in the composition/formulation is present in a range of 0.1% to 5.0% by weight of the total composition/formulation.

In some embodiment of the invention, the solvent is selected from water, alcohol, isopropyl 10 alcohol, propylene glycol, mineral oil, benzyl alcohol, benzyl benzoate, flavoured glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight.

The additional additives include a polymer, a plasticizer, a sweetener or a taste-masking agent, and a powdered flavor, a preservative, a colorant, a surfactant, and other excipients. The powdered flavor composition includes a flavourant associated with a solid carrier.

Taste-masking agents are selected from Fructose/starch, sucrose, maltodextrin, saccharine, sorbitol, magnesium citrate, sodium citrate, trehalose, maltose, isomalt, xylitol and beta-cyclodextrin.

Coating materials are selected from synthetic polymers, shellac, corn protein (zein) or other polysaccharides, gelatin, fatty acids, waxes, shellac, plastics, and plant fibers and like thereof are used.

In a preferred embodiment of the invention, the additives are used in a range of 1% to 20% w/w of unit dose.

In a preferred embodiment of the invention, amount of additives are present in a range of 0.1% to 10% by weight of the composition/formulation.

In yet another embodiment, the invention provides a synergistic composition comprising a therapeutic blend of a biotin-manganese complex and a stabilized oxaloacetate along with pharmaceutical excipients, wherein the pharmaceutical excipients are selected from a diluent, a binder, a lubricant, a glidant, an additive, a surfactant, a stabilizer or mixtures thereof.

In a preferred embodiment, the invention provides the novel and stable composition wherein the pharmaceutically acceptable excipients are selected from a group consisting of the diluent is present in a range of 1 to 30%; the binder present is present in a range of 0.1 to 25%; the lubricant is present in a range of 0.1 to 10.0%; the glidant is present in a range of 0.1 to 5.0%; the additive is present in a range of 1 to 10%; the surfactant is present in a range of 0.1 to 5.0%; the stabilizer is present in a range of 0.1 to 5.0%; %; the antioxidant is present in a range of 0.1 to 5.0%; and the plasticizer is present in a range of 0.1 to 5.0%; by weight of total composition.

In another preferred embodiment, the present medicinal composition/formulation is formulated for oral administration. Specifically, the solid medicinal compositions, are in the form of tablets, capsules, pills, hard capsules filled with liquids or solids, soft capsules, sachets, powders, granules, suspensions, solutions, or modified release formulations. Formulations of the present invention suitable for oral administration are presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

In further embodiment compositions containing compounds of the present invention, can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof.

The magnitude of a prophylactic or therapeutic dose typically varies with the nature and severity of the condition to be treated and the route of administration. The dose, and perhaps the dose frequency, will also vary according to the age, body weight and response of the individual patient.

In general, the total daily dose (in single or divided doses) ranges from about 1 mg per day to about 2500 mg per day, preferably about 10 mg per day to about 1000 mg per day. In some embodiments, the total daily dose can range from about 5 mg to about 4000 mg per day, and preferably about 5 mg to about 2000 mg per day.

In certain embodiments, the invention provides the potent synergistic medicinal composition wherein the effective unit dose for an oral administration is formulated in a range of 10 to 1000 mg.

It is further recommended that children, patients over 60 years old, initially receive low doses and that the dosage be titrated based on individual physiological responses and/or pharmacokinetics.

It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust or terminate therapy in conjunction with an individual patient's response.

The use of any and all examples, or exemplary language (e.g., such as) provided herein, is intended merely to better illuminate the invention, and does not pose a limitation on the scope of the invention unless otherwise claimed.

Various other examples of compositions and modifications or adaptations thereof can be devised by a person skilled in the art after reading the foregoing preferred embodiments without departing from the scope of the invention. All such further examples, modifications and adaptations are included within the scope of the invention.

It will be appreciated by those versed in the art that the present invention makes available novel and useful nutraceutical compositions and nutraceutical acceptable salts thereof, which have neuroprotective effects in several administration forms. Also, it will be understood by those with knowledge in the dietary supplement and nutraceutical art, that many embodiments of this invention may be made without departing from the scope of the invention, and the invention is not to be construed as limited, as it embraces all equivalents therein.

The invention may be further illustrated by the following examples, which are for illustrative purposes only and should not be construed as limiting the scope of the invention in anyway.

The present disclosure is therefore to be considered as in all respects illustrative and not restrictive, the scope of the invention being indicated by the appended claims and examples, and all changes or alterations which come within the ambit of equivalency are intended to be encompassed therein.

EXAMPLES

Having described the basic aspects of the present invention, the following non-limiting examples illustrate specific embodiments thereof. Those skilled in the art will appreciate that many modifications may be made in the invention without changing the essence of invention.

Example-1

| i. Composition 1: Synergistic blend | |
| --- | --- |
| Ingredient | w/w % |
| (Magnesium 2-acetylamino ethane sulfonic acid) 2-methyl-4-aminomethyl-5-hydroxymethyl-3-Pyridinol dihydrochloride | 25%-99% 0.1%-60% |

| ii. Composition 2: Tablet/Capsule | |
| --- | --- |
| Ingredient | w/w % unit dose |
| Magnesium 2-acetylamino ethane sulfonic acid | 66% ± 6 |
| 2-methyl-4-aminomethyl-5-hydroxymethyl-3-Pyridinol dihydrochloride | 29% ± 9 |
| Excipient | 5-20% |
| Average Weight | 100% |

| iii. Composition 3: Tablet/Capsule | |
| --- | --- |
| Ingredient | w/w % unit dose |
| Magnesium 2-acetylamino ethane sulfonic acid | 60% |
| 2-methyl-4-aminomethyl-5-hydroxymethyl-3-Pyridinol dihydrochloride | 33% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Antioxidant | 0.1-5% |
| Solvents | QS |

| iv. Composition 4: Tablet/Capsule | |
| --- | --- |
| Ingredient | mg per unit dose |
| (Magnesium 2-acetylamino ethane sulfonic acid) | 350 |
| 2-methyl-4-aminomethyl-5-hydroxymethyl-3-Pyridinol dihydrochloride | 50 |
| Sodium Benzoate | 1-5 |
| Magnesium Stearate | 1-10 |
| Hydroxypropyl Methylcellulose | 1-10 |
| Microcrystalline Cellulose | 1-20 |
| PVP K-30 | 5-10 |
| Silicon dioxide | 1-10 |
| Polysorbate 20 | 1-10 |
| Sorbitol | 1-20 |
| Propylene Glycol | QS |
| Water | QS |
| Average weight | |

| v. Composition 5: Tablet/Capsule | |
| --- | --- |
| Ingredient | mg per unit dose |
| (Magnesium 2-acetylamino ethane sulfonic acid) | 500 |
| 2-methyl-4-aminomethyl-5-hydroxymethyl-3-Pyridinol dihydrochloride | 2 |
| Sodium Benzoate | 1-10 |
| Magnesium Stearate | 1-20 |
| Sodium ascorbate | 2-10 |
| Microcrystalline Cellulose | 2-20 |
| Colloidal Silicon dioxide | 5-15 |
| Hydroxypropyl Methylcellulose | 2-10 |
| triethyl citrate | 2-10 |
| PVP K-30 | 5-10 |
| Talc | 1-10 |
| Phosphatidylcholine | 1-10 |
| Mannitol | 5-20 |
| Alcohol | QS |
| Water | QS |
| Average weight | 500-560 mg | vi. Composition 6: Tablet/Capsule

| Ingredient | mg per unit dose |
| --- | --- |
| (Magnesium 2-acetylamino ethane sulfonic acid) | 500 |
| 2-methyl-4-aminomethyl-5-hydroxymethyl-3-Pyridinol dihydrochloride | 1 |
| Sodium Benzoate | 1-5 |
| Microcrystalline Cellulose | 2-20 |
| Silicon dioxide | 1-10 |
| Hydroxypropyl Methylcellulose | 2-10 |
| Stearic acid | 2-10 |
| Dibasic calcium phosphate | 1-20 |
| Magnesium citrate | 5-10 |
| Talc | 1-10 |
| Phosphatidylcholine | 1-10 |
| Polydextrose | 1-10 |
| Water | QS |
| Average weight | 500-550 mg | vii. Composition 7: Tablet/Capsule

| Ingredient | mg per unit dose |
| --- | --- |
| Magnesium 2-acetylamino ethane sulfonic acid | 100 |
| 2-methyl-4-aminomethyl-5-hydroxymethyl-3-Pyridinol dihydrochloride | 100 |
| Microcrystalline Cellulose | 1-10 |
| Silicon dioxide | 1-10 |
| Ethyl Cellulose | 1-10 |
| Hydroxypropyl Methylcellulose | 1-10 |
| Magnesium Stearate | 2-10 |
| Polyvinylpyrrolidone | 1-10 |
| Talc | 1-10 |
| Polysorbate 20 | 1-10 |
| Mannitol | 1-10 |
| IPA | QS |
| Water | QS |
| Average weight | 220-260 mg | viii. Composition 8: Tablet/Capsule

| Ingredient | mg per unit dose |
| --- | --- |
| Magnesium 2-acetylamino ethane sulfonic acid | 100 |
| 2-methyl-4-aminomethyl-5-hydroxymethyl-3-Pyridinol dihydrochloride | 10 |
| Silicon Dioxide | 1-10 |
| Medium-chain triglycerides | 1-5 |
| Microcrystalline Cellulose | 2-20 |
| Dibasic Calcium Phosphate | 2-20 |
| Magnesium Stearate | 2-10 |
| Croscarmellose sodium | 2-10 |
| Polyvinylpyrrolidone | 1-20 |
| Talc | 1-10 |
| Corn Starch | 1-10 |
| Sodium ascorbate | 1-10 |
| Propylene glycol | 1-10 |
| Water | QS |
| Average weight | 150-200 mg | ix. Composition 9: Tablet/Capsule

| Ingredient | mg per unit dose |
| --- | --- |
| Magnesium 2-acetylamino ethane sulfonic acid | 250 |
| 2-methyl-4-aminomethyl-5-hydroxymethyl-3-Pyridinol dihydrochloride | 10 |
| Microcrystalline Cellulose | 1-10 |
| Colloidal silicon dioxide | 1-10 |
| Hydroxypropyl Methylcellulose | 1-10 | ix. Composition 9: Tablet/Capsule

| Ingredient | mg per unit dose |
| --- | --- |
| Magnesium citrate | 2-10 |
| Polyvinylpyrrolidone | 1-10 |
| Calcium Phosphate | 1-10 |
| Ascorbic Acid | 1-10 |
| Phosphatidylcholine | 1-10 |
| Talc | 1-5 |
| Sucrose | 1-10 |
| Mannitol | 1-10 |
| MCT | 1-10 |
| Average weight | 250-350 mg | x. Composition 10: Tablet/Capsule

| Ingredient | mg per unit dose |
| --- | --- |
| Magnesium 2-acetylamino ethane sulfonic acid | 80 |
| 2-methyl-4-aminomethyl-5-hydroxymethyl-3-Pyridinol dihydrochloride | 150 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Ascorbic Acid | 1-10 |
| Medium chain Triglyceride | 1-10 |
| Talc | 1-5 |
| Dextrose | 1-10 |
| Mannitol | 1-10 |
| Water | QS |
| Average weight | 250-350 mg | xi. Composition 11: Tablet/Capsule

| Ingredient | mg per unit dose |
| --- | --- |
| (Magnesium 2-acetylamino ethane sulfonic acid) | 200 |
| 2-methyl-4-aminomethyl-5-hydroxymethyl-3-Pyridinol dihydrochloride | 100 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Polysorbate 80 | 1-10 |
| Talc | 1-5 |
| Sucrose | 1-10 |
| Mannitol | 1-10 |
| Water | QS |
| Average weight | 320-370 mg | xii. Composition 12: Tablet/Capsule

| Ingredient | mg per unit dose |
| --- | --- |
| (Magnesium 2-acetylamino ethane sulfonic acid) | 500 |
| 2-methyl-4-aminomethyl-5-hydroxymethyl-3-Pyridinol dihydrochloride | 25 |
| Sodium Benzoate | 5 |
| Microcrystalline Cellulose | 1-10 |
| Colloidal Silicon dioxide | 1-10 |

-continued

| xii. Composition 12: Tablet/Capsule | |
| --- | --- |
| Ingredient | mg per unit dose |
| Hydroxypropyl cellulose | 1-10 |
| Magnesium Stearate | 2-10 |
| Calcium Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-10 |
| Talc | 1-5 |
| Dextrose | 1-10 |
| Mannitol | 1-10 |
| Water | QS |
| Average weight | 550-600 mg |

Example 2

In Vitro Study

The purpose of this study is to evaluate cytoprotective activity of test substance against advanced glycation end product (AGE) induced oxidative stress in Human Keratinocytes cell line (HaCaT).

Summary

The test substance was evaluated for its in vitro potency to protect against AGE induced oxidative stress in HaCaT cell line. In the given experimental conditions, treatment with the test substance protected the HaCaT cells against AGE induced oxidative stress.

Method

Outline of the Method:

The in vitro cytotoxicity was performed on Human Keratinocytes (HaCaT) cell line to find the non-toxic concentrations of the test substances by MTT assay and evaluate their cytoprotective activity against advanced glycation end product (AGE) induced oxidative stress in Human Keratinocytes.

Preparation of Test Solution:

About 10 mg of the test substance was dissolved separately with 1 mL DMEM-HG supplemented with 2% inactivated FBS to obtain a stock solution of 10 mg/mL concentration and sterilized by $0.22\mu$ syringe filtration. Dilute the stock to desired concentrations for carrying out further studies.

Cell Line and Culture Medium:

HaCaT (Human Keratinocytes cells) was procured from AddexBio, U.S. Stock cells were cultured in DMEM-HG supplemented with 10% inactivated Fetal Bovine Serum (FBS), penicillin (100 IU/mL), streptomycin (100 $\mu$g/mL) and amphotericin B (5 $\mu$g/mL) in humidified atmosphere of 5% $CO_2$ at 37° C. until confluent. The cells were dissociated with TPVG solution (0.2% trypsin, 0.02% EDTA, 0.05% glucose in PBS). The stock cultures were grown in 25 $cm^2$ culture flasks and all experiments were carried out in 96 microtitre plates (Tarsons India Pvt. Ltd., Kolkata, India).

Cytotoxicity Studies:

The cell culture monolayer was trypsinized and the cell count was adjusted to $1.0\times10^5$ cells/mL using DMEM-HG containing 10% FBS. To each well of the 96 well microtitre plate, 0.1 mL of the diluted cell suspension was added. After 24 hours, when a partial monolayer was formed, the supernatant was flicked off, the monolayer was washed once with PBS and 100 $\mu$L of different concentrations of test substance was added. The plate was then incubated at 37° C. for 24 hours in a 5% $CO_2$ atmosphere, and microscopic examination was carried out and observations were noted after 24 h time.

MTT Assay:

After 24 hours of incubation, the drug solution in the wells was discarded and 50 $\mu$L of MTT in DPBS was added to each well. The plate was gently shaken and incubated for 3 hours at 37° C. in a 5% $CO_2$ atmosphere. The supernatant was removed and 100 $\mu$L of DMSO was added and the plate was gently shaken to solubilize the formed formazan. The absorbance was measured using a micro plate reader at a wavelength of 570 nm. The percentage growth inhibition was calculated using the standard formula. The concentration of test substance, needed to inhibit the growth of the cell by 50% i.e., CTC50 values were generated from the dose-response curves.

| Study Design: | | |
| --- | --- | --- |
| Sl. No. | Group | Dose and Treatment |
| 1. | Cell Control | No treatment |
| 2. | Positive Control (Methylglyoxal- 300 $\mu$M) | Cells were treated only with Methylglyoxal |
| 3. | Reference standard Metformin (5 mg) | Cells were treated with Methylglyoxal and test substance |
| 4. | Test I- Magnesium 2-acetylamino ethane sulfonic acid (3.5 mg) | Cells were treated with Methylglyoxal and test substance |
| 5. | Test II- 2-methyl-4-aminomethyl-5-hydroxymethyl-3-Pyridinol (0.5 mg) | Cells were treated with Methylglyoxal and test substance |
| 6. | Test III- Magnesium 2-acetylamino ethane sulfonic acid & 2-methyl-4-aminomethyl-5-hydroxymethyl-3-Pyridinol (5 mg & 0.02 mg) | Cells were treated with Methylglyoxal and test substances |
| 7. | Test IV- Magnesium 2-acetylamino ethane sulfonic acid & 2-methyl-4-aminomethyl-5-hydroxymethyl-3-Pyridinol (0.2 mg & 0.2 mg) | Cells were treated with Methylglyoxal and test substances |
| 8. | Test V- Magnesium 2-acetylamino ethane sulfonic acid & 2-methyl-4-aminomethyl-5-hydroxymethyl-3-Pyridinol (3.5 mg & 0.5 mg) | Cells were treated with Methylglyoxal and test substances |

Sample Treatment:

The monolayer cell culture was trypsinized and the cell count was adjusted to $1.5\times10^5$ cells/mL using DMEM-HG containing 10% FBS. To each well of the 6 well plates, 2 mL of the diluted cell suspension was added. After 24 hours, when a partial monolayer was formed, supernatant was removed and washed the monolayer once with PBS and 1 mL of different test concentrations and combinations of test substances were added. The plate was then incubated at 37° C. for 24 h in a 5% $CO_2$ atmosphere, and microscopic examination was carried out and observations were noted after 24 hours time.

Estimation of Cell Viability by Tryphan Blue Dye Exclusion Assay:

After 24 hours, the media was discarded and cells were trypsinized and pelleted by centrifugation, suspended in 1 mL of fresh media and performed dye exclusion test, i.e., mixed equal volume of cells suspended media and Tryphan blue.

Viable and non-viable cells were counted using haemocytometer and values were recorded, and then percentage cell viability was calculated.

Result:

TABLE 1

Percentage of cytotoxicity of the test substance in HaCaT cells

| Name of Test Sample | Test Concentration (mg/mL) | % Cytotoxicity |
|---|---|---|
| 2-methyl-4-aminomethyl-5-hydroxymethyl-3-Pyridinol | 5 | 76.01 |
| | 4 | 75.82 |
| | 3 | 67.46 |
| | 2 | 67.04 |
| | 1 | 63.38 |
| | 0.5 | 25.59 |
| | 0.25 | 5.68 |
| | 0.125 | 4.55 |

TABLE 2

Percentage of viable cells using tryphan blue exclusion assay in HaCaT cell

| Group | % Viability |
|---|---|
| Methylglyoxal-300 μM | 38.77 |
| Metformin-5 mg | 70.79 |
| Test I- Magnesium 2-acetylamino ethane sulfonic acid -3.5 mg | 42.39 |
| Test II- 2-methyl-4-aminomethyl-5-hydroxymethyl-3-Pyridinol -0.5 mg | 41.23 |
| Test III- Magnesium 2-acetylamino ethane sulfonic acid- 5 mg + 2-methyl-4-aminomethyl-5-hydroxymethyl-3-Pyridinol - 0.02 mg | 62.02 |
| Test IV- Magnesium 2-acetylamino ethane sulfonic acid- 0.2 mg + 2 methyl-4-aminomethyl-5-hydroxymethyl-3-Pyridinol - 0.2 mg | 92.54 |
| Test V- Magnesium 2-acetylamino ethane sulfonic acid- 3.5 mg + 2-methyl-4-aminomethyl-5-hydroxymethyl-3-Pyridinol -0.5 mg | 48.86 |

Discussion and Conclusion:

In the current study, the effect of test compounds for cytoprotective activity against advanced glycation end product (AGE) induced oxidative stress in Human Keratinocytes cell line (HaCaT) was analyzed. Among all the groups tested, Test IV with the combination of Magnesium 2-acetylamino ethane sulfonic acid+2-methyl-4-aminomethyl-5-hydroxymethyl-3-Pyridinol-(0.2:0.2 mg) exhibited the highest percentage of cell viability with 92.54%. However, test III and V with the combination of Magnesium 2-acetylamino ethane sulfonic acid+2-methyl-4-aminomethyl-5-hydroxymethyl-3-Pyridinol (5 mg: 0.02 mg) and (3.5 mg: 0.5 mg) have also shown percentage of cell viability with 62.02% and 48.86% respectively. Test I [Magnesium 2-acetylamino ethane sulfonic acid (3.5 mg)] and Test II [2-methyl-4-aminomethyl-5-hydroxymethyl-3-Pyridinol (0.5 mg)] have shown percentage of cell viability with 42.39% and 41.23% respectively. For the positive control (Methylglyoxal-300 μM), the percentage of cell viability observed is about 38.77%. Most of the test groups and combinations tested have shown considerable increase in cell viability against the positive control (Methylglyoxal).

The evidence from this study concluded that the combination of Magnesium 2-acetylamino ethane sulfonic acid and 2-methyl-4-aminomethyl-5-hydroxymethyl-3-Pyridinol in specific weigh ratio are good cytoprotective agent against AGE induced oxidative stress.

The invention claimed is:

1. A synergistic bioactive composition for inhibiting vascular calcification, comprising a therapeutically active exogenous combination of an effective amount of magnesium 2-acetylamino ethane sulfonic acid and 2-methyl-4-aminomethyl-5-hydroxymethyl-3-pyridinol or salts thereof, along with at least one pharmaceutically acceptable excipient wherein the magnesium 2-acetylamino ethane sulfonic acid and 2-methyl-4-aminomethyl-5-hydroxymethyl-3-pyridinol or salts thereof are present in a weight ratio of 1:0.002 to 1:1.8 along with the at least one pharmaceutically acceptable excipient, and wherein the magnesium 2-acetylamino ethane sulfonic acid is white crystalline and present in a range of 25% to 99% by weight of the total composition and the 2-methyl-4-aminomethyl-5-hydroxymethyl-3-pyridinol salt is white crystalline and present in a range of 0.1% to 60% by weight of the total composition.

2. The synergistic bioactive composition as claimed in claim 1, wherein the at least one pharmaceutically acceptable excipient is selected from a group consisting of: a diluent in a range of 1 to 30%, a binder present in a range of 0.5 to 25%, a lubricant in a range of 0.1 to 10.0%, a glidant in a range of 0.1 to 5.0%, an additive in a range of 0.1 to 10%, a surfactant in a range of 0.1 to 5.0%, a stabilizer in a range of 0.1 to 5.0%, an antioxidant in a range of 0.1 to 5.0%, and a plasticizer in a range of 0.1 to 5.0%, by weight of the total composition.

3. The synergistic bioactive composition as claimed in claim 1, wherein an effective unit dose for an oral administration is formulated in a range of 10 to 1000 mg.

4. The synergistic bioactive composition as claimed in claim 3, wherein the effective unit dose is useful for treating disorders or diseases selected from the group consisting of hypertension, diabetes, chronic kidney diseases, diabetic nephropathy, coronary artery diseases, cardiovascular diseases, kidney function decline, dialysis vintage, disordered mineral metabolism, elevated serum phosphate levels, elevated serum calcium levels, elevated parathyroid hormone levels, changes in vitamin D metabolism, elevated FGF 23 levels, inflammation and oxidative stress, osteogenesis factors (Cbfa1), heart attack, heart failure, diabetes stroke, dementia, renal insufficiency, inadequate blood supply to arms and legs, peripheral artery disease (PAD), loss of elasticity of arteries, increase in pulse pressure, development of left ventricular hypertrophy (LVH), heart failure (HF), lower coronary artery perfusion and myocardial ischemia, impaired calcium-phosphate metabolism, diastolic dysfunction, cardiac valve calcification, ischemic heart disease, and episodes of cardiac failure.

5. The synergistic bioactive composition as claimed in claim 1, wherein the composition improves cell viability from 48% to 93%.

*　*　*　*　*